(12) United States Patent
Cavanagh et al.

(10) Patent No.: US 10,813,770 B2
(45) Date of Patent: Oct. 27, 2020

(54) DEVICES AND METHODS FOR METATARSOPHALANGEAL ARTHROPLASTY PROCEDURES

(71) Applicant: University of Washington, Seattle, WA (US)

(72) Inventors: Peter R. Cavanagh, Seattle, WA (US); William R. Ledoux, Seattle, WA (US); Bruce J. Sangeorzan, Seattle, WA (US)

(73) Assignees: United States Government as Represented by the Department of Veterans Affairs, Washington, DC (US); University of Washington, Seattle, WA (US)

( * ) Notice: Subject to any disclaimer, the term of this patent is extended or adjusted under 35 U.S.C. 154(b) by 169 days.

(21) Appl. No.: 15/542,009

(22) PCT Filed: Jan. 12, 2016

(86) PCT No.: PCT/US2016/013101
§ 371 (c)(1),
(2) Date: Jul. 6, 2017

(87) PCT Pub. No.: WO2016/115172
PCT Pub. Date: Jul. 21, 2016

(65) Prior Publication Data
US 2017/0367838 A1 Dec. 28, 2017

Related U.S. Application Data

(60) Provisional application No. 62/102,886, filed on Jan. 13, 2015.

(51) Int. Cl.
*A61F 2/42* (2006.01)
*A61F 2/30* (2006.01)

(52) U.S. Cl.
CPC .. *A61F 2/4225* (2013.01); *A61F 2002/30578* (2013.01); *A61F 2002/30878* (2013.01);
(Continued)

(58) Field of Classification Search
CPC ............ A61F 2/4225; A61F 2002/4233; A61F 2002/30578; A61F 2002/30902
See application file for complete search history.

(56) References Cited

U.S. PATENT DOCUMENTS 4,156,296 A 5/1979 Johnson et al.
4,787,908 A 11/1988 Wyss et al.
(Continued)

FOREIGN PATENT DOCUMENTS

EP 1897509 A1 3/2008
WO 2016115172 A1 7/2016

OTHER PUBLICATIONS

Brewster M., "Does total joint replacement or arthrodesis of the first metatarsophalangeal joint yield better functional results? A systematic review of the literature." J Foot Ankle Surg., 2010; 49(6): 546-552.
(Continued)

*Primary Examiner* — Bruce E Snow
*Assistant Examiner* — Melissa A Hoban
(74) *Attorney, Agent, or Firm* — Ballard Spahr LLP (57) ABSTRACT

The present technology relates generally to devices and methods for arthroplasty procedures. In some embodiments, for example, a device is disclosed for use during an arthroplasty procedure of a joint of a patient, the joint extending between a first joint end of a first bone and an abutting second joint end of a second bone of the patient. The device includes an end plate configured and arranged for disposing over the first joint end of the first bone, a longitudinal plate extending from the end plate and configured and arranged
(Continued)

for disposing along a medial, longitudinal surface of the first bone, and a stem extending from the end plate and suitable for extending along an intra-medullary canal of the first bone. When installed, at least one fastener extends at least partially through the first bone and couples the longitudinal plate to the first bone.

17 Claims, 7 Drawing Sheets

(52) U.S. Cl.
 CPC .............. *A61F 2002/30902* (2013.01); *A61F 2002/4233* (2013.01)

(56) References Cited

U.S. PATENT DOCUMENTS

| | | | |
|---|---|---|---|
| 7,291,175 | B1 | 11/2007 | Gordon |
| 7,491,220 | B2 | 2/2009 | Coughln |
| 8,162,996 | B2 | 4/2012 | Schelling |
| 8,167,918 | B2 | 5/2012 | Strnad et al. |
| 8,292,966 | B2 | 10/2012 | Morton |
| 8,303,666 | B2 | 11/2012 | Vanasse |
| 2005/0085819 | A1 | 4/2005 | Ellis et al. |
| 2006/0241608 | A1 | 10/2006 | Myerson et al. |
| 2007/0299533 | A1 | 12/2007 | Reiley |
| 2008/0051912 | A1 | 2/2008 | Hollawell |
| 2008/0195215 | A1 | 8/2008 | Morton et al. |
| 2011/0087334 | A1 | 4/2011 | Morton et al. |
| 2011/0093084 | A1 | 4/2011 | Morton et al. |
| 2011/0093085 | A1 | 4/2011 | Morton et al. |
| 2012/0065689 | A1 | 3/2012 | Prasad et al. |
| 2012/0109322 | A1 | 5/2012 | Gonzalez-Hernandez et al. |
| 2013/0172942 | A1 | 7/2013 | Lewis et al. |
| 2014/0121779 | A1 | 5/2014 | Gonzalez-hernandez |
| 2014/0316530 | A1 | 10/2014 | Early et al. |

OTHER PUBLICATIONS

D'Angelantonio AM, et al., "Master techniques in digital arthrodesis." Clinics in Podiatric Medicine and Surgery, 2012;29(1):21-40.

Hromádka R, et al., "MEDIN implant of the first metatarsophalangeal joint." Acta Chir Orthop Traumatol Cech 2012;79(2):124-130.

Konkel KF, et al., "Results of metallic Hemi-Great Toe Implant for Grade III and early Grade IV hallux rigidus." Foot Ankle Int, 2009;30(7):653-660.

Maffulli N, et al., "Quantitative review of operative management of hallux rigidus." Br Med Bull 2011;98:75-98.

Mann RA, et al., "Hallux rigidus: treatment by cheilectomy." J Bone Joint Surg Am 1988; 70(3):400-406.

Nagy MT, et al., "Second-Generation Ceramic First Metatarsophalangeal Joint Replacement for Hallux Rigidus." Foot Ankle Int. Jul. 1, 2014;35(7):690-698.

Papagelopoulos PJ, et al., "Survivorship analysis of implant arthroplasty for the first metatarsophalangeal joint." Clin Orthop Relat Res 1994;(302):164-172.

Raikin SM, et al., "Comparison of arthrodesis and metallic hemiarthroplasty of the hallux metatarsophalangeal joint." J Bone Joint Surg Am 2007;89(9):1979-1985.

Shereff MJ, et al., "Hallux rigidus and osteoarthrosis of the first metatarsophalangeal joint." J Bone Joint Surg Am 1998;80(6):898-908.

Smith K, et al., "Mechanical comparison of cortical screw fixation versus locking plate fixation in first metatarsal base osteotomy." J Foot Ankle Surg. Sep.-Oct. 2014;53(5):529-33.

Swanson AB, et al., "Use of grommets for flexible hinge implant arthroplasty of the great toe." Clin Orthop Relat Res 1997;(340):87-94.

Van Saase et al., "Osteoarthritis and obesity in the general population. A relationship calling for an explanation." J Rheumatol 1988;15(7):1152-1158.

International Search Report and Written Opinion in International Application No. PCT/US17/43639, dated Oct. 6, 2017, 8 pages.

International Search Report and Written Opinion dated Mar. 10, 2016 in PCT/US2016/013101, 9 pages.

DEVICES AND METHODS FOR METATARSOPHALANGEAL ARTHROPLASTY PROCEDURES

CROSS-REFERENCE TO RELATED APPLICATION

This application claims the benefit of U.S. Provisional Patent Application No. 62/102,886, filed Jan. 13, 2015, which is incorporated herein by reference in its entirety.

STATEMENT OF GOVERNMENT SUPPORT

This invention was made with government support under Grant No. R21 AR069283, awarded by the National Institutes of Health. The government has certain rights in the invention.

TECHNICAL FIELD

This invention was made with the assistance, at least in part, from United States government support awarded by the Department of Defense under PR043074 and W81XWH-05-1-0389 and by the Department of Veterans Affairs under A6404R and B3463R. This invention was made with government support under Grant No. R21 AR069283, awarded by the National Institutes of Health. The government has certain rights in the invention.

BACKGROUND

Osteoarthritis ("OA"), particularly OA in the main joint of the great toe (i.e., the first metatarsophalangeal joint ("MTPJ1"), is a significant public health problem. According to one study, by 60 years of age the prevalence of radiographically-confirmed MTPJ1 OA is present in approximately 46% of women and 32% of men. Typical presentations include hallux rigidus or hallux limitus with a painful joint, hallux-sesamoid arthritis, hallux valgus, and inflammatory arthritis. Pathology of this small joint can have a major effect on quality of life because patient mobility is compromised by pain and lack of motion.

DETAILED DESCRIPTION

The present disclosure relates generally to devices and methods for arthroplasty of a metatarsophalangeal joint. In particular, the disclosed technology is directed to devices and associated techniques for use during an arthroplasty procedure of the metatarsophalangeal joint. As noted above, osteoarthritis (OA), particularly in the main joint of the great toe (the first metatarsophalangeal joint (MTPJ1)) is a challenging joint to treat. The goals of treatment for OA of the MTPJ1 are to reduce pain and restore mobility of the MTPJ1. When conservative treatment has failed, the two most common surgical options for treatment of OA are removal of damaged articular cartilage and bone (cheilectomy) and, for more severe cases, complete fixation of the joint with trans-articular screws or plates (arthrodesis). Neither of these approaches have high rates of patient satisfaction—particularly among women, who find footwear choices limited after the main toe joint is fixed.

The MTPJ1 is also a challenging joint to replace. The presently available devices to replace all or part of MTPJ1 can be classified into three groups: (1) Single hemi-arthroplasty (e.g., a Futura™ metal hemi toe device); (2) Unconstrained modular arthroplasty for both joint components (e.g., a Medin™ MTP Toe Joint replacement device); or (3) Flexible hinge joints (e.g., a Swanson™ Flexible Hinge Toe). None of these devices, however, have received widespread acceptance from the foot and ankle surgical community; arthrodesis remains the treatment of choice for most surgeons.

Further challenges with replacing the MTPJ1 often arise because there is typically insufficient bone available for fixation using conventional methods, and the loads on the joint are large. At least one study indicates that the median failure/complication rate is 15%, but the upper end of the range is an alarming 93%. In a recent systematic review of outcomes, one author concluded that: "arthrodesis achieves better functional outcomes than total joint replacement" and that "advances still need to be achieved to produce a more successful and anatomical prosthesis that could be functionally superior to an arthrodesis." Brewster, Mark. "Does total joint replacement or arthrodesis of the first metatarsophalangeal joint yield better functional results? A systematic review of the literature." *The Journal of Foot and Ankle Surgery* 49.6 (2010): 546-552.

An examination of the failure patterns in conventional MTPJ1 joint replacements shows that the most common reported causes of failure are loosening, misalignment, or migration. This is not surprising when the usual techniques of fixation are considered—the components are press- or screw-fitted into the medullary cavity of at least one bone abutting the joint of interest, with or without a polyethylene insert, after reaming of the bone.

Devices configured in accordance with the present technology for use during an arthroplasty procedure of a metatarsophalangeal joint of a patient are expected to address the shortcomings of conventional devices. In one embodiment, for example, a device for use during an arthroplasty procedure of a metatarsophalangeal joint includes an end plate coupled configured and arranged for disposing over a first joint end of a first bone, a longitudinal plate coupled to the end plate and configured and arranged for disposing along a medial, longitudinal surface of the first bone, and a stem coupled to the end plate and suitable for extending along an intra-medullary canal of the first bone. At least one fastener couples the longitudinal plate to the stem, the at least one fastener extending at least partially through a longitudinal surface of the first bone.

Further embodiments of the present technology are also directed to methods of performing an arthroplasty procedure on a joint of a human patient. One method can include, for example, removing a portion of a first joint end of a first bone and coupling an implant to the first joint end of the first bone. The implant is coupled such that (a) a stem of the implant is disposed within an intra-medullary canal of the first bone, (b) an end plate of the implant is disposed over the first joint end of the first bone, and (c) a longitudinal plate of the implant is disposed along a medial, longitudinal surface of the first bone. The method can further include extending a fastener between the longitudinal plate and the stem, with the fastener passing through the longitudinal surface of the first bone.

Further specific details of several embodiments of the present technology are described below with reference to FIGS. 1-4D. Although many of the embodiments are described below with respect to devices, systems, and methods for arthroplasty procedures, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

As used herein, the terms "distal" and "proximal" refer to the location of the referenced element with respect to the tarsal bones of the patient's foot near the ankle. "Proximal" refers to a location closer to the tarsal bones/ankle, and "distal" refers to a location farther away from the tarsal bones/ankle toward the phalanges (the bones of the toes).

Selected Embodiments of Devices and Methods for Arthroplasty Procedures

Figure 1:
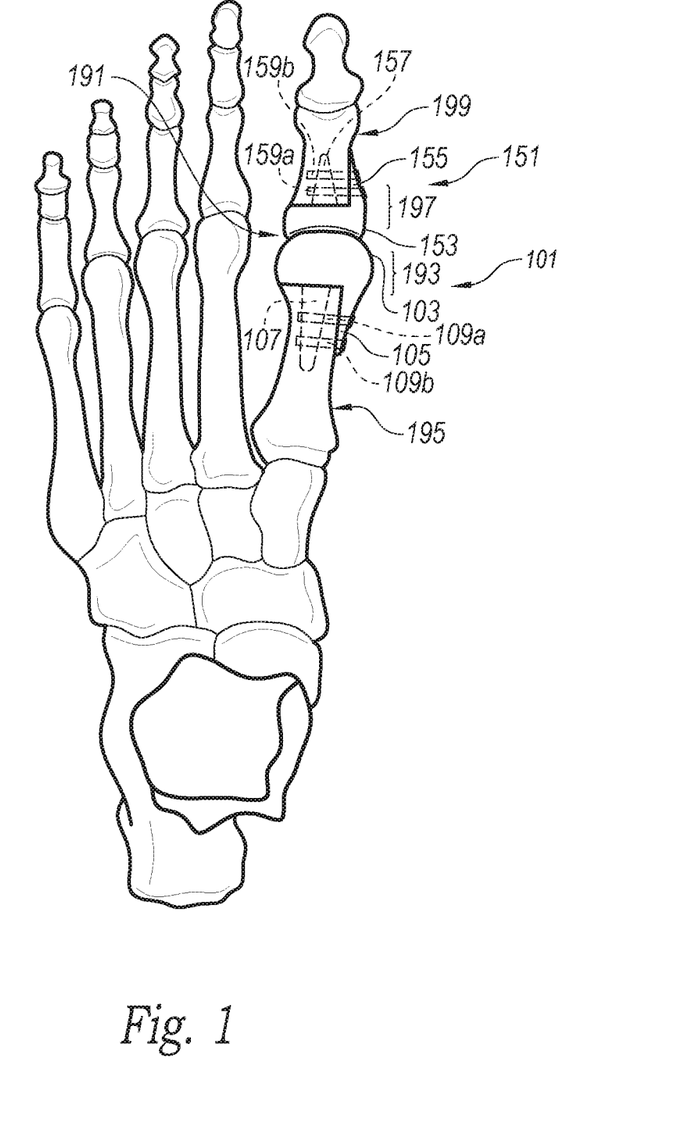
FIG. 1 is a top plan view of first and second arthroplasty devices implanted in a left human foot and configured in accordance with an embodiment of the present technology.

FIG. 1 is a top plan view of first and second arthroplasty devices 101 and 151 implanted in a left foot of a human patient and configured in accordance with an embodiment of the present technology. As illustrated, the first arthroplasty device 101 and the second arthroplasty device 151 are implanted at the metatarsophalangeal joint (MTPJ1) 191 of the great toe. In particular, the first arthroplasty device 101 is coupled to a distal end region 193 of a metatarsal bone 195 and the second arthroplasty device 151 is coupled to a proximal end region 197 of a proximal phalanx bone 199 of the patient.

The first arthroplasty device 101 includes an end plate 103 disposed over the distal end region 193 of the metatarsal bone 195. A longitudinal plate 105 extends from the end plate 103 proximally away from the end plate 103 along a medial surface of the metatarsal bone 195. A stem 107 (shown in broken lines) also extends proximally from the end plate 103 along the intramedullary canal of the metatarsal bone 195. Fasteners 109a and 109b (shown in broken lines) can be inserted through holes (FIGS. 2A and 2B) in the longitudinal plate 105 and the stem 107 and obtain purchase in the lateral cortex of the metatarsal bone 195. In some embodiments, the fasteners 109a-b are locking screws. In other embodiments, however, the fasteners 109a-b may have a different configuration.

The second arthroplasty device 151 can be configured similarly to the first arthroplasty device 101. For example, the second arthroplasty device 151 includes an end plate 153 disposed over the proximal end region 197 of the proximal phalanx bone 199. The end plate 153 of the second arthroplasty device 151 is configured to engage with the end plate 103 of the first arthroplasty device 101. A longitudinal plate 155 extends distally away from the end plate 153 along a medial surface of the proximal phalanx bone 199. A stem 157 extends distally from the end plate 153 along the intramedullary canal of the proximal phalanx bone 199. Fasteners 159a and 159b (shown in broken lines) extend through the longitudinal plate 155 and the stem 157 and couple the longitudinal plate 155 to the proximal phalanx bone 199. For example, the fasteners 159a and 159b can be inserted through holes (not shown) in the longitudinal plate 155 and the stem 157 and gain purchase in the lateral cortex of the proximal phalanx bone 199.

The surfaces of the end plates 103 and 153 are complementary to allow for the surfaces to mate with one another while allowing the two to articulate with respect to one another. In some embodiments, for example, the surface of the end plate 103 of the first arthroplasty device 101 is convex and the surface of the end plate 153 of the second arthroplasty device 151 is concave. In other embodiments, however, the shapes of the end surfaces can be reversed (i.e., the surface of end plate 103 may be concave and surface of end plate 153 may be convex). In another embodiment, the surface of the end plate 103 of the first arthroplasty device 101 has a shape corresponding to the natural shape of the metatarsal bone 195 and the surface of the end plate 153 of the second arthroplasty device 151 has a shape corresponding to the natural shape of the proximal phalanx bone 199. In some embodiments, the complementary shapes for the articular surfaces may be patient-specific surfaces based on previously obtained information from a CT scan or other imaging technique. While such personalization may be attractive in some cases, in other embodiments generic articular surface shapes over an anticipated size range are used.

It will be appreciated that although FIG. 1 illustrates a foot with both the first arthroplasty device 101 and the second arthroplasty device 151 installed, in other embodiments only one of the two devices (the first arthroplasty device 101 or the second arthroplasty device 151) may be installed (e.g., hemiarthroplasty). Further, while the arrangement in FIG. 1 shows the longitudinal plates 105 and 155 of the first and second arthroplasty devices 101 and 151, respectively, installed on a medial side of the corresponding bones, in other embodiments the devices could be attached to other surfaces of the bone.

FIGS. 2A-2D are enlarged isometric, top, proximal, and medial views, respectively, of the first arthroplasty device 101 of FIG. 1 adjacent to a prepared metatarsal bone 195. For purposes of clarity, the metatarsal bone 195 is omitted from the proximal view in FIG. 2C, and fasteners 109a-b are omitted from FIGS. 2C and 2D. Referring to FIGS. 2A-2D together, the first arthroplasty device 101 includes end plate 103 and longitudinal plate 105 extending proximally away from the end plate 103. The stem 107 extends proximally away from the end plate 103, approximately parallel to the longitudinal plate 105. In the illustrated embodiment, the end plate 103, longitudinal plate 105, and stem 107 are integrally formed. In other embodiments, however, the components of the first arthroplasty device 101 may be individual components that are coupled together before installation.

The longitudinal plate 105 includes one or more holes or apertures 110 (two are shown) for receiving fastener(s), such as fasteners 109a-b, to secure the first arthroplasty device 101 in place relative to the bone 195. The stem 107 can also include one or more corresponding holes or apertures 111 aligned with the holes 110 to receive the fastener(s) and allow the fastener(s) to pass through to obtain purchase in the opposite bone cortex. In some embodiments, the holes 111 in the stem 107 may be oversized relative to the holes 110 and fasteners 109a-b. Although the holes 110 are shown with a raised profile in the illustrated embodiment, in other embodiments the holes 110 may be countersunk relative to the surface of the longitudinal plate 105 such that when the fasteners 109a-b are installed therethrough, the fastener heads are flush with the surface of the longitudinal plate 105.

Figure 2A:
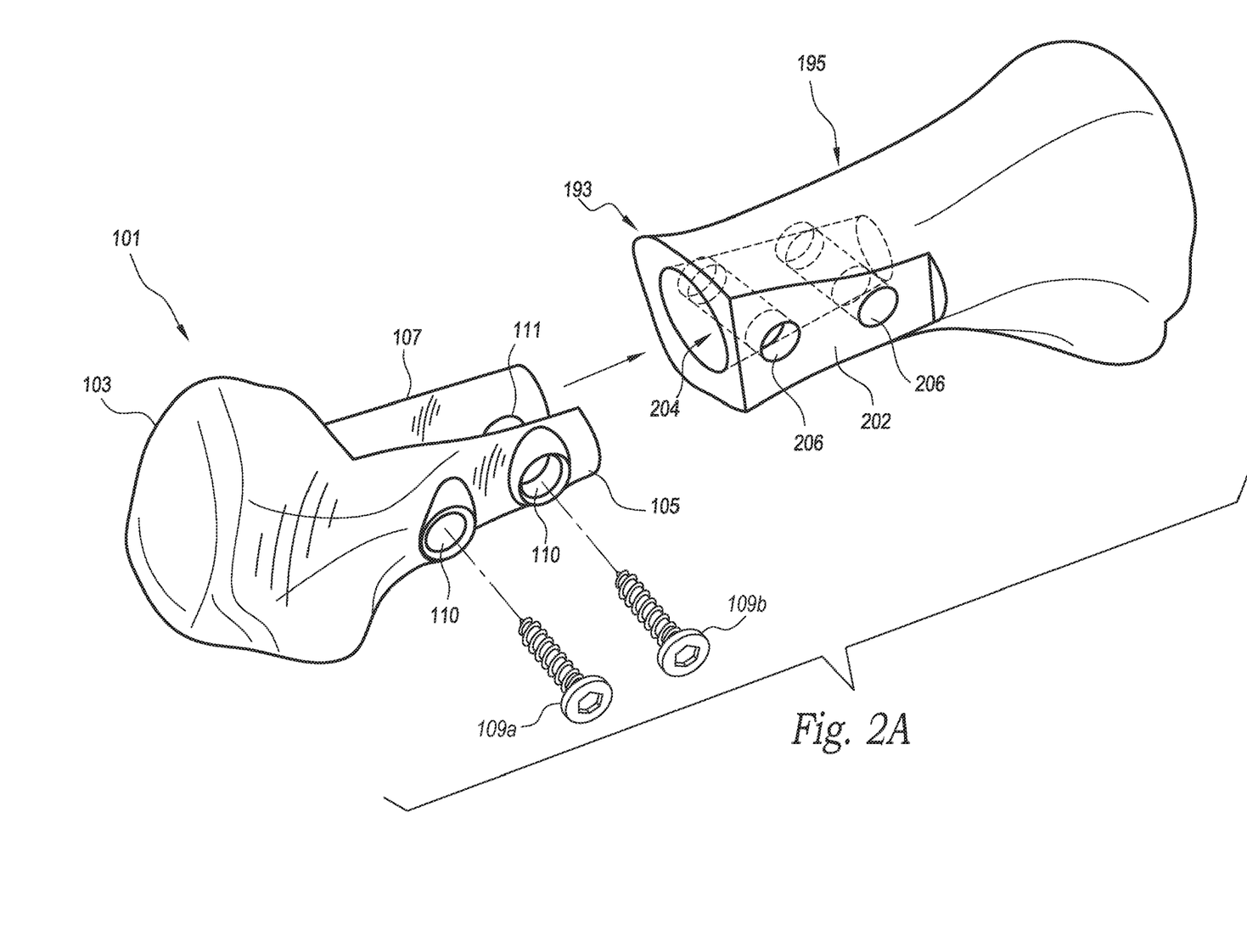
FIGS. 2A-2D illustrate various views of the first arthroplasty device of FIG. 1 configured in accordance with an embodiment of the present technology.
Figure 2B:
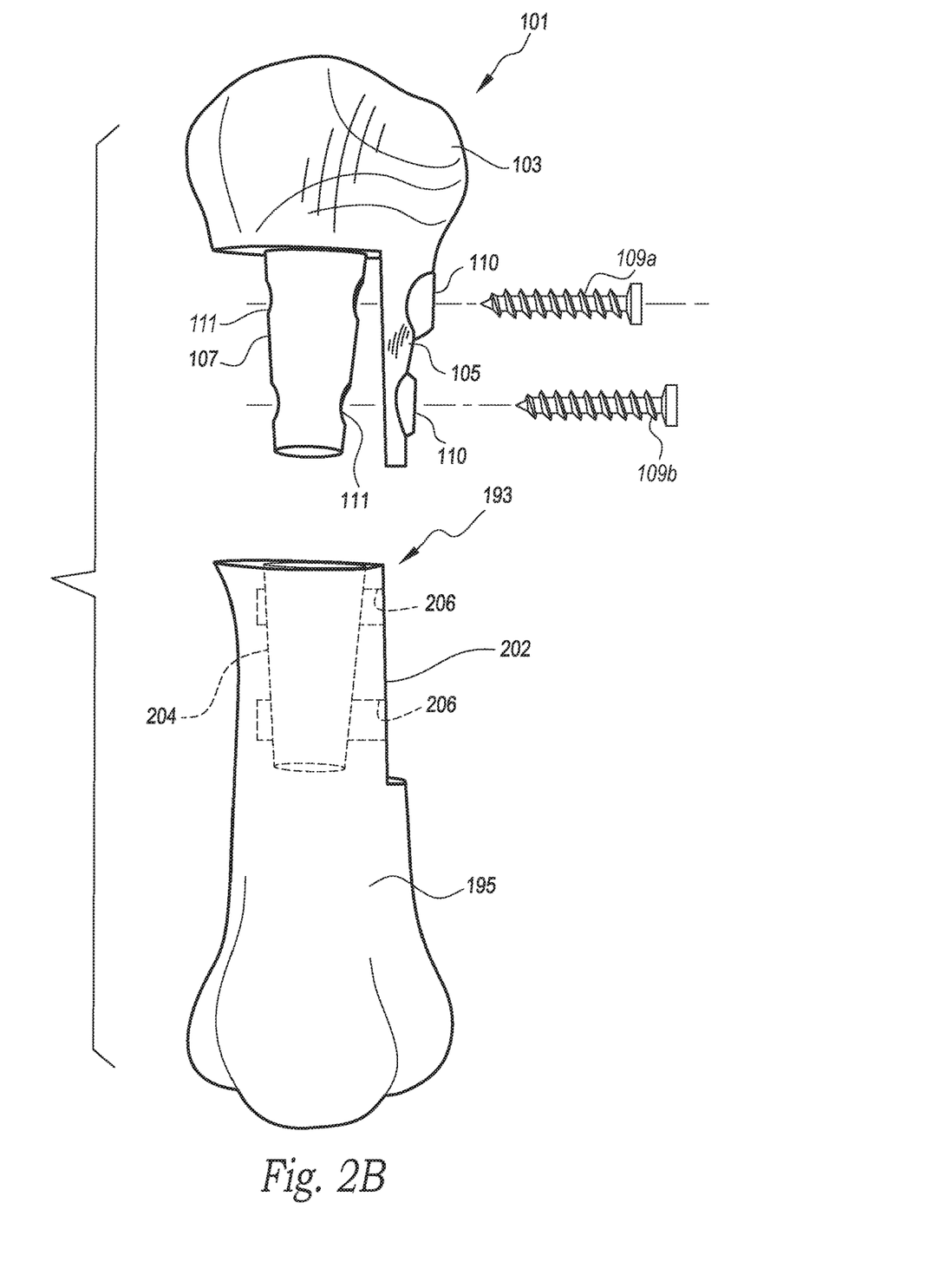
Figure 2C:
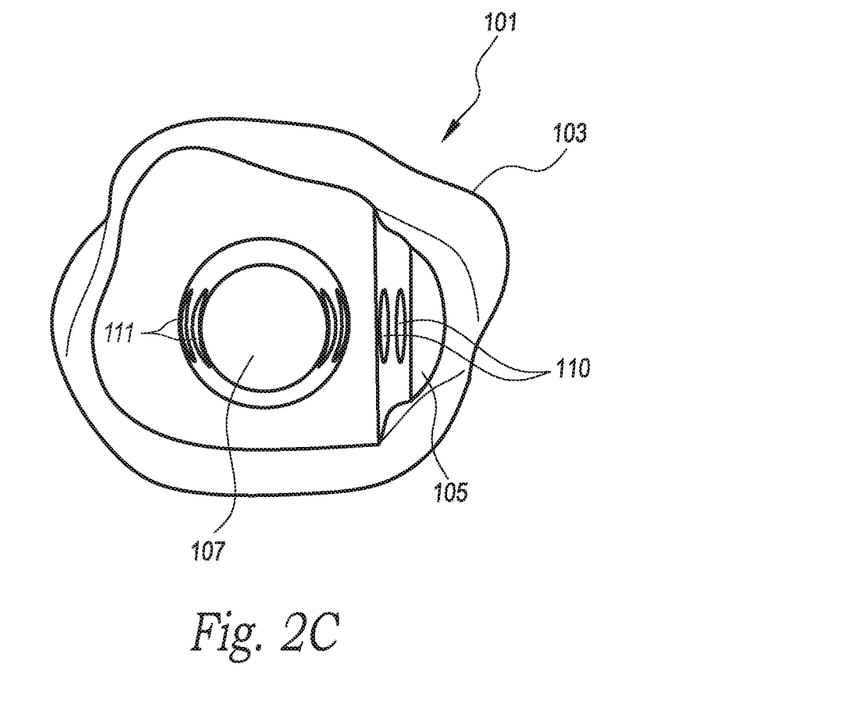
Figure 2D:
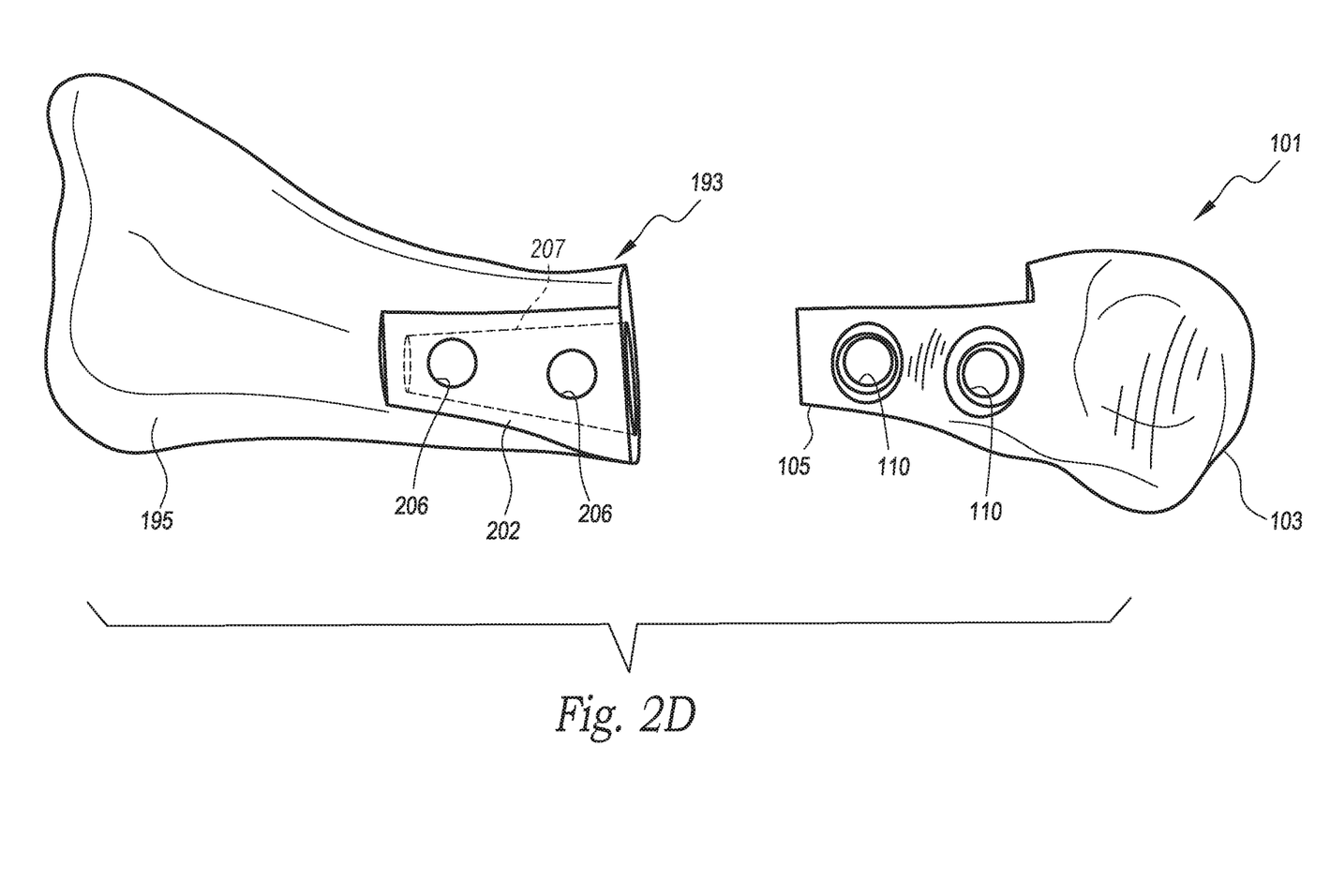

As best seen in FIGS. 2A and 2B, in order to prepare the metatarsal bone 195 to receive the first arthroplasty device 101, a surgical template or guide (not shown) may be used. For example, the surgical template can be used by the surgeon when removing/shaping the distal end region 193 of the bone 195 that will be replaced by the end plate 103 of the first arthroplasty device 101. The surgical template can also be used to shape a medial portion 202 of the bone 195 to accommodate the longitudinal plate 105 of the first arthroplasty device 101. Further, a reamer may be used to create a void 204 (e.g., a conical void) shaped and sized for receiving the stem 107 therein when the first arthroplasty device 101 is mated with the metatarsal bone 195.

Guide hole(s) 206 for fastener insertion may also be formed in the metatarsal bone 195 substantially perpendicular to the long axis of the bone 195, and configured to intersect with the void 204. In the illustrated embodiment, two guide holes 206 have been formed and shaped/sized to correspond to holes 110 when the first arthroplasty device 101 is installed.

During installation, the first arthroplasty device 101 is mated with the prepared metatarsal bone 195. In at least some embodiments, the first arthroplasty device 101 may tapped into place. When the first arthroplasty device 101 in in place relative to the bone 195, the fasteners 109a and 109b are inserted through the holes 110 in the longitudinal plate 105 and through the guide holes 206 in the metatarsal bone 195. As best seen in FIGS. 2A and 2B, the fasteners 109a-b are sized and shaped to extend through the holes 110 and the oversized holes 111 in the stem to couple the longitudinal plate 105 to the metatarsal bone 195. When installed (and as noted above with reference to FIG. 1), the fasteners 109a-b also extend partially through the metatarsal bone 195 and gain purchase in the lateral cortex of the metatarsal bone 195.

One feature of the first arthroplasty device 101 is that, when installed, the stem 107 and longitudinal plate 105 are coupled together via at least one fastener 109. This feature is expected to reduce or inhibit the problems experienced by many conventional devices associated with loosening, misalignment, and/or migration of the implant. Further, because the fasteners 109a-b gain purchase though a relatively significant portion of the bone 195, the first arthroplasty device 101 is expected to be able to handle the large loads on the MTPJ1 joint with less complications/failures than conventional devices.

Figure 3A:
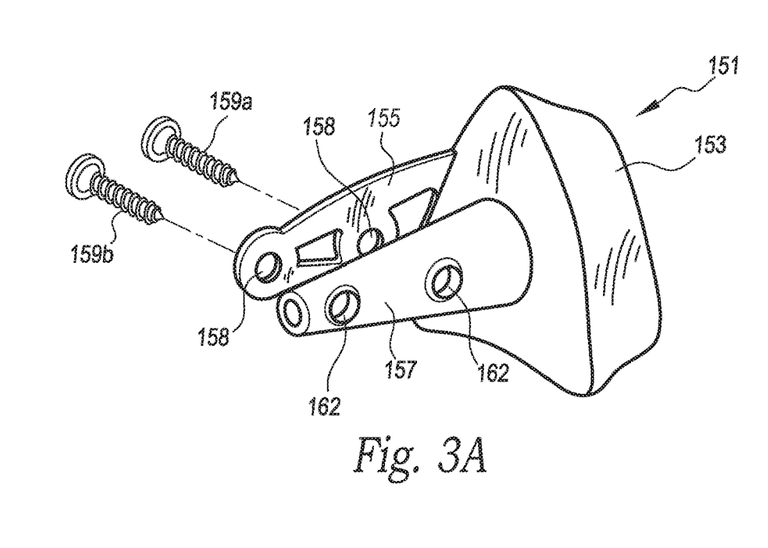
FIGS. 3A-3D illustrate various views of the second arthroplasty device of FIG. 1 configured in accordance with an embodiment of the present technology.
Figure 3B:
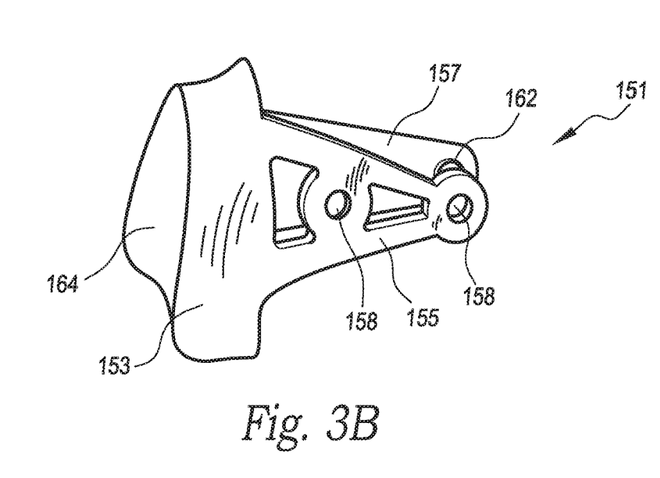

FIGS. 3A-3D illustrate various views of the second arthroplasty device 151 configured in accordance with an embodiment of the present technology. In particular, FIGS. 3A and 3B are enlarged, isometric views of the second arthroplasty device 151 before installation. For purposes of clarity, the proximal phalanx bone 199 is omitted from FIGS. 3A and 3B. Referring to FIGS. 3A and 3B together, the second arthroplasty device 151 includes a number features similar to the features of the first arthroplasty device 101 described above with reference to FIGS. 1-2D. For example, as noted previously, the second arthroplasty device 151 includes end plate 153 and longitudinal plate 155 extending distally away from the end plate 153. The end plate 153 of the second arthroplasty device 151 has a concave arrangement configured to engage with the convex surface of the end plate 103 of the first arthroplasty device 101 (FIG. 1). The second arthroplasty device 151 also includes stem 157 extending away from the end plate 153, approximately parallel to the longitudinal plate 155. In the illustrated embodiment, the end plate 153, longitudinal plate 155, and stem 157 of the second arthroplasty device 151 are integrally formed. In other embodiments, however, the components of the second arthroplasty device 151 may be individual components that are coupled together before installation. Further, in the illustrated embodiment there are voids in the longitudinal plate 155, but in other embodiments there may be no voids in the longitudinal plate 155.

Figure 3C:
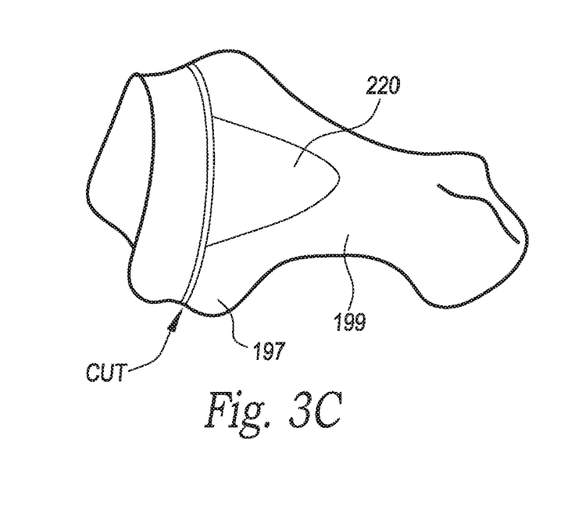
Figure 3D:
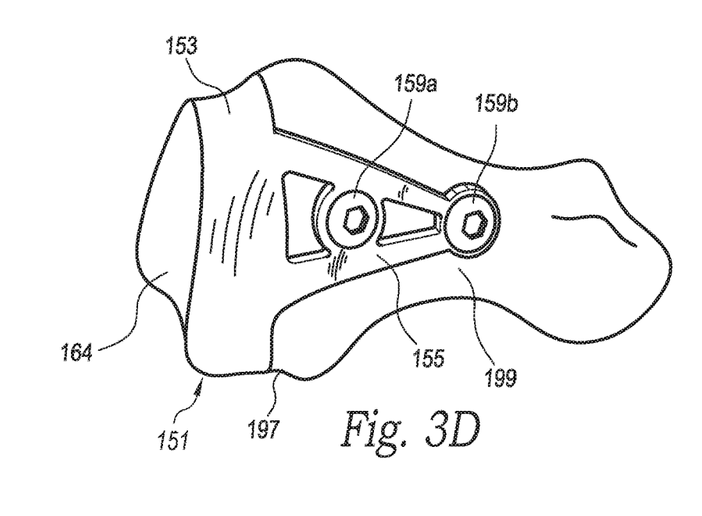

The longitudinal plate 155 includes one or more holes or apertures 158 (two are shown) for receiving fastener(s), such as fasteners 159a-b, to secure the second arthroplasty device 151 in place relative to the bone 199 (FIG. 3D). The stem 157 can also include one or more corresponding holes or apertures 162 aligned with the holes 158 to receive a portion of the fastener(s) 159.

FIG. 3C is an exploded isometric view of the proximal phalanx bone 199 prior to receiving the second arthroplasty device 151, and FIG. 3D illustrates the second arthroplasty device 151 installed with the proximal phalanx bone 199. Referring first to FIG. 3C, a surgical template or guide (not shown) may be used to prepare the proximal phalanx bone 199 for installation. The process can be similar to that described above with reference to the metatarsal bone 195. For example, the surgical template can be used for cutting/shaping the proximal end region 197 of the bone 199 to receive the second arthroplasty device 151. A medial portion 220 of the bone 199 may also shaved/shaped to receive the longitudinal plate 155. Further, a void (not seen in FIG. 3C) can be created in the bone 199 to receive the stem 157 therein during installation. Guide holes (not seen in FIGS. 3C and 3D) are also formed and shaped/sized to correspond to holes 158/162 when the second arthroplasty device 151 is installed.

As best seen in FIG. 3D, once the second arthroplasty device 151 is mated with and positioned as desired relative to the proximal end region 197 of the bone 199, fasteners 159a-b can be installed through the holes 158 in the longitudinal plate 155 and the corresponding holes 162 in the stem 157 (FIGS. 3A and 3B). Although the fasteners 159a-b are shown with slightly raised profile after installation in FIG. 3D, in other embodiments the holes 158 (FIG. 3B) may be countersunk relative to the surface of the longitudinal plate 155 such that when the fasteners 159a-b are installed therethrough, the fastener heads are flush with the surface of the longitudinal plate 155.

As with the first arthroplasty device 101 described above, the fasteners 159a and 159b gain purchase in the lateral cortex of the proximal phalanx bone 199 and help reduce/inhibit loosening, misalignment, and/or migration of the device after implantation.

Figure 4A:
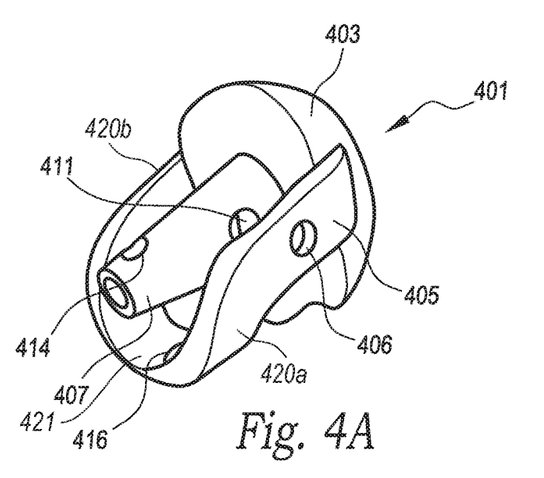
FIGS. 4A-4D illustrate various views of a first arthroplasty device configured in accordance with another embodiment of the present technology.
Figure 4B:
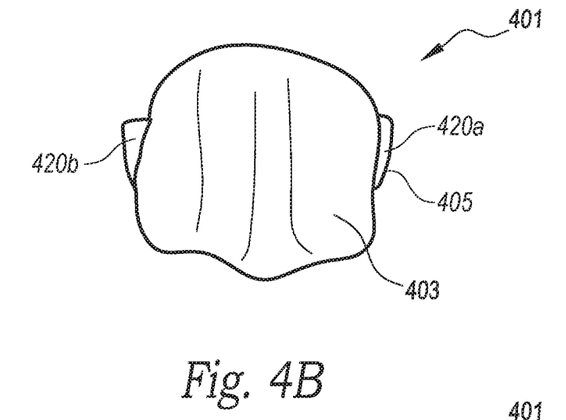
Figure 4C:
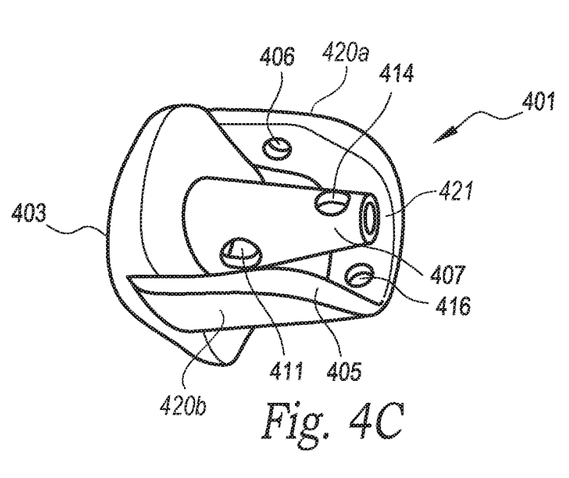
Figure 4D:
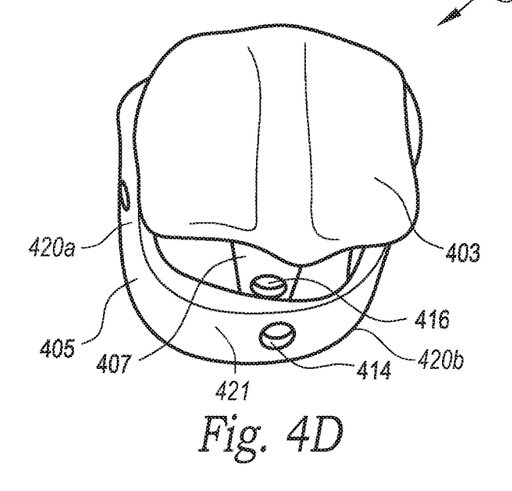

FIGS. 4A-4D illustrate various views of an arthroplasty device 401 configured in accordance with another embodiment of the present technology. The arthroplasty device 401 is similar to the first arthroplasty device 101 described above with reference to FIGS. 1-2D, expect that the arthroplasty device 401 includes a longitudinal plate 405 having a different configuration than the longitudinal plate 105 of the device 101. In particular, as best seen in FIGS. 4A and 4C, the longitudinal plate 405 extends from end cap 403 and includes first and second longitudinal sides 420a and 420b generally parallel with a stem 407, and an arcuate bridge portion 421 extending between the first and second longitudinal 420a and 420b and beneath the stem 407. The longitudinal plate 405 is configured such that, when implanted the sides 420a-b and bridge portion 421 extend over medial, dorsal, and plantar surfaces of the metatarsal bone (not shown).

The arthroplasty device 401 also includes holes or apertures 406 and 416 extending through the first longitudinal side 420a and bridge portion 421, respectively. The holes 406 and 416 are aligned with corresponding holes or apertures 411 and 414, respectively, through the stem 407. As with the first and second arthroplasty devices 101 and 151 described above, the arthroplasty device 401 is configured to receive one or more fasteners (not shown) through corresponding holes 406 and/or 416 to couple the device 401 to the metatarsal bone during installation.

The arthroplasty devices 101/151/401, including the fasteners 109/159 and other referenced fasteners described herein, can be made of a variety of materials including, for example, biocompatible materials such as stainless steel, titanium, and other biocompatible and rigid materials suitable for use in surgical implants.

Further, although the description above refers to the MTPJ1 joint for illustrative purposes, embodiments of the first and second arthroplasty devices 101 and 151 described herein can be suitable for use along any suitable patient joint, for example other metatarsophalangeal joints of the foot, metacarpophalangeal joints of the hand, and any other suitable joint. Moreover, it will be appreciated that the disclosed arthroplasty devices can be modified in many different ways to better accommodate different joints and different anatomies within individual patients. Additionally, although the longitudinal plate is shown on the medial side in the embodiments describe above with reference to FIGS. 1-3D, in other embodiments the longitudinal plate may attached to other surfaces of the bone in lieu of (or in addition to) the medial surface.

ADDITIONAL EXAMPLES

1. A device for use during an arthroplasty procedure of a joint of a patient, the joint extending between a first joint end of a first bone and an abutting second joint end of a second bone of the patient, the device comprising:
   - an end plate configured and arranged for disposing over the first joint end of the first bone;
   - a longitudinal plate extending from the end plate and configured and arranged for disposing along a medial, longitudinal surface of the first bone;
   - a stem extending from the end plate and suitable for extending along an intra-medullary canal of the first bone; and
   - at least one fastener for coupling the longitudinal plate to the first bone,
   - wherein, when the device is installed, the at least one fastener extends at least partially through the longitudinal surface of the first bone.

2. The device of example 1 wherein:
   the joint is a metatarsophalangeal joint;
   the first bone is a metatarsus bone;
   the second bone is an abutting proximal phalanx bone; and
   the end plate is convex.

3. The device of example 1 wherein:
   the joint is a metatarsophalangeal joint;
   the first bone is a proximal phalanx bone of a foot;
   the second bone is an abutting metatarsal bone; and
   the end plate is concave.

4. The device of any one of examples 1-3, further comprising a first hole in the longitudinal plate and a second hole in the stem, wherein, when the device is installed, the fastener extends through the first and second holes.

5. The device of example 4, further comprising:
   a third hole in the longitudinal plate and a fourth hole in the stem; and
   a second fastener coupling the longitudinal plate to the stem, wherein the second fastener is configured to extend through the third and fourth holes.

6. The device of any one of examples 1-5 wherein the fastener is a locking screw.

7. The device of any one of examples 1-6, further comprising a second longitudinal plate coupled to the end plate and configured and arranged for disposing along the medial, longitudinal surface of the first bone circumferentially opposite to the first longitudinal plate along the medial, longitudinal surface of the first bone, and wherein, when the device is installed, the fastener couples the first and second longitudinal plates to the first bone.

8. The device of any one of examples 1-7 wherein end plate, the longitudinal plate, and the stem comprise at least one of titanium or stainless steel.

9. The device of any one of examples 1-8 wherein the end plate, the longitudinal plate, and the stem are integrally formed.

10. The device of any one of examples 1-9 wherein the stem is tapered.

11. A device for use during an arthroplasty procedure of a joint of a patient, the joint extending between a first joint end of a first bone and an abutting second joint end of a second bone of the patient, the device comprising:
    - an end plate configured to be disposed over the first joint end of the first bone;
    - a longitudinal plate extending from the end plate and configured to be disposed along a medial, longitudinal surface of the metatarsus bone, the longitudinal plate having a hole formed therein; and
    - a stem extending from the end plate and suitable for extending along an intra-medullary canal of the first bone, the stem having a second hole formed therein, and wherein the first hole and the second hole are aligned.

12. The device of example 11, further comprising a fastener for coupling the longitudinal plate to the first bone, and wherein, when the device is installed, the fastener extends through the first hole and the second hole, passing at least partially through the longitudinal surface of the first bone.

13. The device of example 11 wherein:
    the joint is a metatarsophalangeal joint;
    the first bone is a metatarsus bone;
    the second bone is an abutting proximal phalanx bone; and
    the end plate is convex.

14. The device of example 11 wherein:
    the joint is a metatarsophalangeal joint;
    the first bone is a proximal phalanx bone of a foot;
    the second bone is an abutting metatarsal bone; and
    the end plate is concave.

15. A method of performing an arthroplasty procedure on a joint of a human patient, the joint extending between a first joint end of a first bone and an abutting second joint end of a second bone of the patient, the method comprising:
    removing a portion of the first joint end of the first bone;
    coupling an implant to the first joint end of the first bone, such that— a stem of the implant is disposed within an intra-medullary canal of the first bone;
an end plate of the implant is disposed over the first joint end of the first bone; and
a longitudinal plate of the implant is disposed along a medial, longitudinal surface of the first bone; and
extending a fastener between the longitudinal plate and the stem, the fastener passing through the longitudinal surface of the first bone.

16. The method of example 15, further comprising reaming the intra-medullary canal of the first bone prior to coupling the implant to the first joint end of the first bone.

17. The method of example 15 or example 16 wherein removing the portion of the first joint end of the first bone comprises cutting the portion of the first joint end of the first bone using a surgical template.

18. The method of example 15 wherein the joint is a metatarsophalangeal joint, the first bone is a metatarsus bone, and the second bone is an abutting proximal phalanx bone.

19. The method of example 15 wherein the joint is a metatarsophalangeal joint, the first bone is a proximal phalanx bone of a foot, and the second bone is an abutting metatarsal bone.

20. The method of any one of examples 15-19, further comprising:
drilling a hole through at least a portion of the first bone prior to extending the fastener; and
passing the fastener through the hole.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for use during an arthroplasty procedure of a joint of a patient, the joint extending between a first joint end of a first bone and an abutting second joint end of a second bone of the patient, the device comprising:
an end plate configured and arranged for disposing over the first joint end of the first bone;
a longitudinal plate extending from the end plate and configured and arranged for disposing along a medial, longitudinal surface of the first bone, the longitudinal plate having a first hole;
a stem extending from the end plate and suitable for extending along an intra-medullary canal of the first bone, the stem having a second hole; and
at least one fastener for coupling the longitudinal plate to the first bone,
wherein, when the device is installed, the at least one fastener extends at least partially through the longitudinal surface of the first bone, and
wherein the end plate has a shape corresponding to a natural shape of an end portion of a metatarsus bone or a proximal phalanx bone of a foot of the patient,
wherein the at least one fastener comprises a first fastener, and wherein, when the device is installed, the first fastener extends through the first and second holes.

2. The device of claim 1 wherein:
the joint is a metatarsophalangeal joint;
the first bone is a metatarsus bone;
the second bone is an abutting proximal phalanx bone; and
the end plate is convex.

3. The device of claim 1 wherein:
the joint is a metatarsophalangeal joint;
the first bone is a proximal phalanx bone of a foot;
the second bone is an abutting metatarsal bone; and
the end plate is concave.

4. The device of claim 1, further comprising:
a third hole in the longitudinal plate and a fourth hole in the stem; and
a second fastener coupling the longitudinal plate to the stem, wherein the second fastener is configured to extend through the third and fourth holes.

5. The device of claim 1 wherein the at least one fastener is a locking screw.

6. The device of claim 1, wherein the longitudinal plate is a first longitudinal plate, wherein the device further comprises a second longitudinal plate coupled to the end plate and configured and arranged for disposing along a second medial, longitudinal surface of the first bone circumferentially opposite to the first longitudinal plate along the medial, longitudinal surface of the first bone, and wherein, when the device is installed, the at least one fastener couples the first and second longitudinal plates to the first bone.

7. The device of claim 1 wherein the end plate, the longitudinal plate, and the stem comprise at least one of titanium or stainless steel.

8. The device of claim 1 wherein the end plate, the longitudinal plate, and the stem are integrally formed.

9. The device of claim 1 wherein the stem has a length, and wherein the stem is tapered moving in a direction away from the end plate along the length of the stem.

10. The device of claim 1, wherein the end plate defines a planar surface configured to engage the first joint end of the first bone, and wherein each of the stem and the longitudinal plate extend perpendicularly to the planar surface of the end plate.

11. The device of claim 1, wherein the stem has a length, and wherein the stem has a central axis with a consistent orientation along the length of the stem.

12. A device for use during an arthroplasty procedure of a joint of a patient, the joint extending between a first joint end of a first bone and an abutting second joint end of a second bone of the patient, the device comprising:
 an end plate configured to be disposed over the first joint end of the first bone;
 a longitudinal plate extending from the end plate and configured to be disposed along a medial, longitudinal surface of the first bone, the longitudinal plate having a hole formed therein; and
 a stem extending from the end plate and suitable for extending along an intra-medullary canal of the first bone, the stem having a second hole formed therein, and wherein the first hole and the second hole are aligned,
 wherein the end plate has a shape corresponding to a natural shape of an end portion of a metatarsus bone or a proximal phalanx bone of a foot of the patient.

13. The device of claim 12, further comprising a fastener for coupling the longitudinal plate to the first bone, and wherein, when the device is installed, the fastener extends through the first hole and the second hole, passing at least partially through the longitudinal surface of the first bone.

14. The device of claim 12 wherein:
 the joint is a metatarsophalangeal joint;
 the first bone is a metatarsus bone;
 the second bone is an abutting proximal phalanx bone; and
 the end plate is convex.

15. The device of claim 12 wherein:
 the joint is a metatarsophalangeal joint;
 the first bone is a proximal phalanx bone of a foot;
 the second bone is an abutting metatarsal bone; and
 the end plate is concave.

16. The device of claim 12, wherein the end plate defines a planar surface configured to engage the first joint end of the first bone, and wherein each of the stem and the longitudinal plate extend perpendicularly to the planar surface of the end plate.

17. The device of claim 12, wherein the stem has a length, and wherein the stem has a central axis with a consistent orientation along the length of the stem.

* * * * *

UNITED STATES PATENT AND TRADEMARK OFFICE
CERTIFICATE OF CORRECTION

PATENT NO. : 10,813,770 B2
APPLICATION NO. : 15/542009
DATED : October 27, 2020
INVENTOR(S) : Peter R. Cavanagh, William R. Ledoux and Bruce J. Sangeorzan Page 1 of 1

It is certified that error appears in the above-identified patent and that said Letters Patent is hereby corrected as shown below:

On the Title Page

"(71) Applicant: University of Washington, Seattle, WA (US)"
Should read:
--(71) Applicants: United States Government as Represented by the Department of Veterans Affairs, Washington, DC (US);
University of Washington, Seattle, WA (US)--

Signed and Sealed this
Fourth Day of January, 2022

Drew Hirshfeld
*Performing the Functions and Duties of the
Under Secretary of Commerce for Intellectual Property and
Director of the United States Patent and Trademark Office*